(12) United States Patent
Oki

(10) Patent No.: US 12,306,158 B2
(45) Date of Patent: May 20, 2025

(54) GAS SENSOR

(71) Applicant: Panasonic Intellectual Property Management Co., Ltd., Osaka (JP)

(72) Inventor: Akio Oki

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 242 days.

(21) Appl. No.: 17/998,656

(22) PCT Filed: Jun. 25, 2021

(86) PCT No.: PCT/JP2021/024122
§ 371 (c)(1),
(2) Date: Nov. 12, 2022

(87) PCT Pub. No.: WO2022/004590
PCT Pub. Date: Jan. 6, 2022

(65) Prior Publication Data
US 2023/0194488 A1    Jun. 22, 2023

(30) Foreign Application Priority Data
Jun. 29, 2020  (JP) .................. 2020-111040

(51) Int. Cl.
*G01N 33/00*  (2006.01)
*G01N 1/22*   (2006.01)
(52) U.S. Cl.
CPC .......... *G01N 33/0016* (2013.01); *G01N 1/22* (2013.01)

(58) Field of Classification Search
CPC .................................................. G01N 33/0016
USPC ....................................................... 73/31.05
See application file for complete search history.

(56) References Cited

U.S. PATENT DOCUMENTS

| 2010/0137733 | A1  | 6/2010 | Wang et al. |
| 2019/0137465 | A1* | 5/2019 | Mizutani ............. G01M 15/102 |
| 2021/0128015 | A1  | 5/2021 | Gerety |
| 2021/0262101 | A1* | 8/2021 | Tanaka .................. C25B 15/087 |

FOREIGN PATENT DOCUMENTS

| JP | 2005-257373 | 9/2005 |
| JP | 2006-119061 | 5/2006 |
| JP | 2009-276309 | 11/2009 |

(Continued)

OTHER PUBLICATIONS

International Search Report of PCT application No. PCT/JP2021/024122 dated Aug. 31, 2021.

*Primary Examiner* — Walter L Lindsay, Jr.
*Assistant Examiner* — Philip T Fadul
(74) *Attorney, Agent, or Firm* — Rimon P.C.

(57) ABSTRACT

A gas sensor includes a suction inlet, a housing communicating with the suction inlet, a gas sensor array disposed in an inside of the housing, and a suction unit disposed at an end of the housing. The suction unit is configured to perform a first suction conveying a gas component in air to the gas sensor array through the suction inlet, and perform a second suction conveying the gas component to the gas sensor array at a flow rate smaller than a flow rate of the first suction. The suction unit is configured to perform the second suction together with the first suction. The gas sensor array is configured to operate while the suction unit performs the second suction.

11 Claims, 5 Drawing Sheets

(56) References Cited

FOREIGN PATENT DOCUMENTS

| JP | 2012-510319 | 5/2012 |
| JP | 2019-086371 | 6/2019 |
| JP | 2020-514730 | 5/2020 |

* cited by examiner

GAS SENSOR

TECHNICAL FIELD

The present disclosure relates to a gas sensor. More particularly, the present disclosure relates to a gas sensor including a suction unit for sucking air including at least a gas component to be detected.

BACKGROUND ART

PTL 1 discloses a combustible gas concentration measuring device including a gas suction means for sucking a combustible gas, an air suction means for sucking air, a mixing portion for mixing the gas with the air, a gas sensor for detecting a concentration of the gas, and a pump for supplying the gas to the gas sensor. In this gas sensor, a gas in a space to be detected is supplied to the gas sensor by the suction means and the pump, and the concentration of the gas can be detected by the gas sensor.

CITATION LIST

Patent Literature

PTL 1: Japanese Patent Laid-Open Publication No. 2006-119061

SUMMARY

A gas sensor includes a suction inlet, a housing communicating with the suction inlet, a gas sensor array disposed in an inside of the housing, and a suction unit disposed at an end of the housing. The suction unit is configured to perform a first suction conveying a gas component in air to the gas sensor array through the suction inlet, and perform a second suction conveying the gas component to the gas sensor array at a flow rate smaller than a flow rate of the first suction. The suction unit is configured to perform the second suction together with the first suction. The gas sensor array is configured to operate while the suction unit performs the second suction.

DESCRIPTION OF EMBODIMENTS

1. Outline

Figure 1:
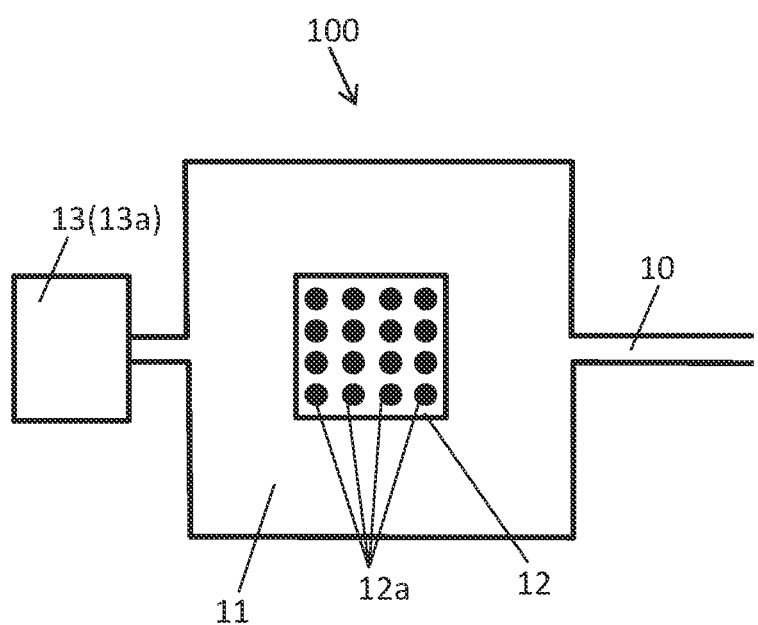
FIG. 1 is a sectional view of a gas sensor in accordance with an exemplary embodiment of the present disclosure.

Gas sensor 100 according to an exemplary embodiment will be described below with reference to FIG. 1. The following exemplary embodiment is only a part of the various exemplary embodiments of the present disclosure. The following exemplary embodiment can be variously modified according to the design and the like as long as an object of the present disclosure can be achieved. Furthermore, the figures described in the following exemplary embodiments are schematic views, and the ratios of sizes and thicknesses of components in the drawings do not necessarily reflect actual dimensions.

Gas sensor 100 according to this exemplary embodiment is configured to detect at least a volatile organic compound to be detected when gas sensor 100 is exposed to an atmosphere including a gas component to be detected, for example, a volatile organic compound. Gas sensor 100 according to this exemplary embodiment includes suction inlet 10, housing 11, gas sensor array 12, and suction unit 13a. Suction unit 13a includes at least one suction device 13. In a first suction, a gas component included in air is conveyed to gas sensor array 12 through suction inlet 10. In a second suction, the gas component included in air is conveyed to gas sensor array 12 at a flow rate smaller than that of the first suction. Suction device 13 performs the first suction and the second suction simultaneously to perform the first suction and the second suction together with each other. The second suction operates gas sensor array 12.

In accordance with this exemplary embodiment, suction inlet 10 communicates with housing 11. Air including a volatile organic compound is sucked to housing 11 through suction inlet 10. Gas sensor array 12 is disposed at an end of housing 11. Gas sensor array 12 detects the volatile organic compound included in air. Suction device 13 sends air to housing 11 through suction inlet 10.

Suction device 13 sucks air from suction inlet 10 in a space including air to be detected. The gas components of the present disclosure may include, for example, odors produced by organisms, foods, machinery, or the human bodies, and gas components which are uncomfortable to human.

In the first suction, suction device 13 sucks air occupying the majority of air conveyed from outside of gas sensor 100 through suction inlet 10 to gas sensor array 12 inside housing 11. Then, the gas component in the sucked air is detected by gas sensor array 12.

Suction device 13 conveys the gas component to gas sensor array 12 in the second suction at a flow rate smaller than that of the first suction. When the second suction is performed together with the first suction, the second suction may modulate the first suction.

Gas sensor array 12 includes plural types of gas sensor elements 12a differently reacting with a gas component, for example, a volatile organic compound. The gas sensor elements 12a is arranged one-, two- or three-dimensionally. In gas sensor array 12 shown in FIG. 1, 16 types of gas sensor elements 12a are arranged two-dimensionally. Signals output from gas sensor array 12 in response to the gas component form patterns in which outputs of gas sensor elements 12a are arranged one-, two- or three-dimensionally. By recognizing the formed patterns by, for example, machine learning algorithm, types and concentrations of the introduced gas components in air are detected. By recognizing the patterns, the combination of the volatile organic compounds in air can be detected.

Gas sensor 100 converts a reaction between the gas component and individual gas sensor elements constituting gas sensor array 12 into an electric signal. In the signal output from a gas sensor element, a reaction with the gas component, in particular, adsorption, can be a large factor. The adsorbing amount n, which is the most important physical quantity in the adsorption phenomenon, is defined by n=F(P,T) where T is an equilibrium temperature and P is pressure.

According to the Bernoulli's theorem, a mechanical energy is conserved in the relation among fluid speed, pressure, and potential of the external force. Therefore, it is generally known that the signal output from the gas sensor element 12a changes depending on a the speed that is a flow rate of a fluid including a gas component. That is, the signal output from gas sensor elements 12a may change due to the flow of air generated by not only the first suction but also the second suction. A signal output from gas sensor element 12a may change due to pressure of air generated by not only the first suction but also the second suction.

Furthermore, in accordance with this exemplary embodiment, gas sensor array 12 employs a machine learning algorithm. In general, it is known that the larger the number of the learning data to be previously acquired is, the more easily the detection accuracy is improved. Suction device 13 conveys air to gas sensor array 12 by the first suction. Furthermore, suction device 13 conveys air to gas sensor array 12 by the second suction at a flow rate smaller than that of the first suction, and by performing the second suction together with the first suction. When a new flow of air by the second suction is added in addition to the flow of air by the first suction, a lot of patterns to be used as learning data can be generated also with respect to the air including the same volatile organic compound. This provides an advantage that the detection accuracy of the volatile organic compound to be detected tends to be more improved as compared with introduction from the outside at a constant flow speed. By adding the change in pressure of new air by the second suction in addition to the change of air pressure by the first suction, plural patterns to be used as learning data can be generated also with respect to air including the same volatile organic compound. This provides an advantage that the detection accuracy of the volatile organic compound to be detected tends to be more improved as compared with introduction from the outside at a constant pressure.

2. Details

Figure 2:
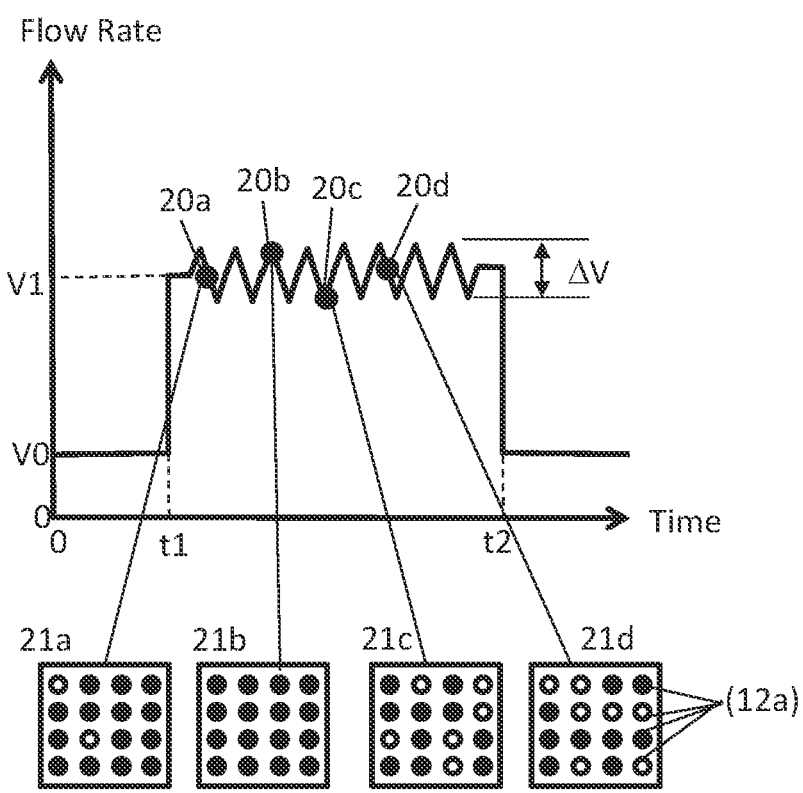
FIG. 2 is an explanatory view of a principle of an operation of the gas sensor, and is a conceptual view showing a flow rate of air sent to a gas sensor array.
Figure 3:
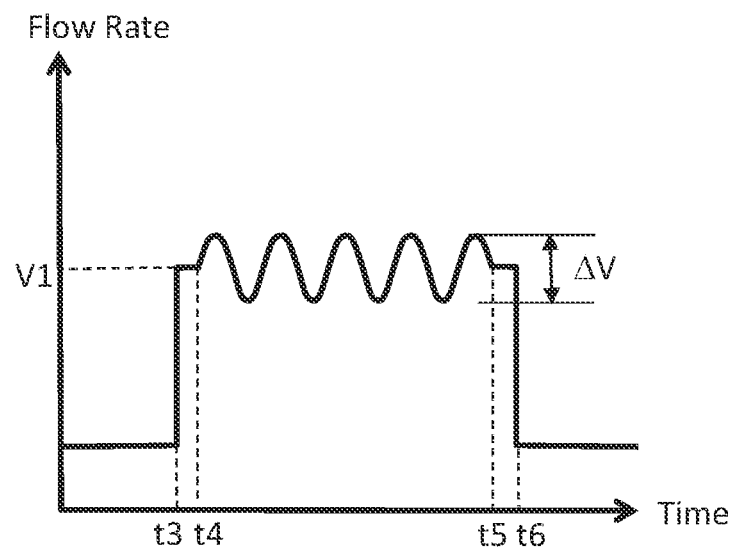
FIG. 3 is an explanatory view of the principle of the operation of the gas sensor, and is a conceptual view showing the flow rate of air sent to the gas sensor array.
Figure 4:
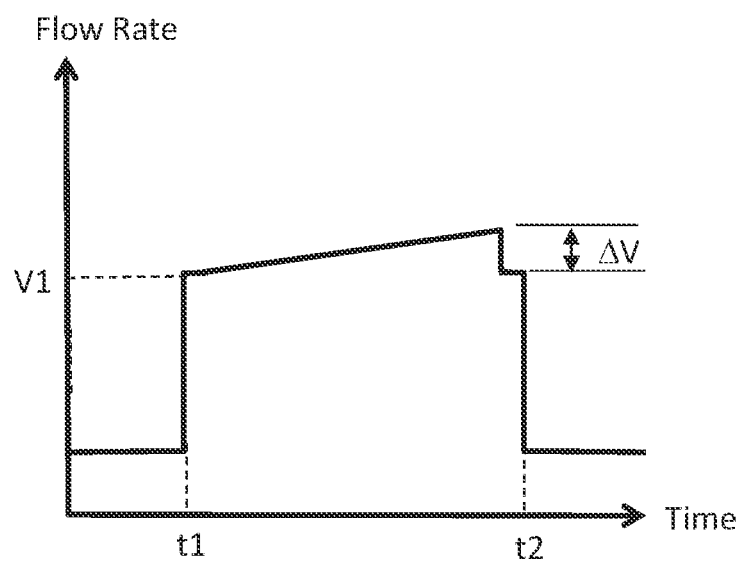
FIG. 4 is an explanatory view of the principle of the operation of the gas sensor, and is a conceptual view showing a flow rate of air sent to a gas sensor array.

Gas sensor 100 according to this exemplary embodiment will be detailed below. FIGS. 2 to 4 are explanatory views showing a principle of an operation of gas sensor 100, and conceptual views showing the flow rate of the air sent to gas sensor array 12. The following description will focus on one gas sensor 100 of the gas sensors including suction devices 13.

Suction inlet 10 is an opening through which housing 11 communicates with the atmospheric air. Suction inlet 10 is an opening through which air including a volatile organic compound to be detected is taken from the outside of gas sensor 100 to housing 11. One suction inlet 10 is shown, but gas sensor 100 may include plural suction inlets 10 for taking up air from the outside of gas sensor 100 to housing 11, respectively. Suction inlet 10 may include a valve or a flow-rate control device for limiting the flow rate.

Housing 11 is a space accommodating air including a volatile organic compound. Furthermore, housing 11 is a space in which gas sensor array 12 is installed inside. Housing 11 may be made of glass, engineering plastics, silicon, metal, carbon material, ceramics, and Teflon® in order to suppress adsorption of a volatile organic compound. Housing 11 may have a cylindrical shape, a spindle shape, or a rectangular parallelopiped shape. The volume of housing 11 is preferably equal to or smaller than 1000 mL, and more preferably, equal to or smaller than 100 mL, for exchanging the conveyed air efficiently.

Gas sensor array 12 includes plural types of gas sensor elements 12a. Each gas sensor element is implemented by, for example, a semiconductor sensor, an electrochemical sensor, a surface acoustic wave element, a field effect transistor biosensor (FET biosensor), a chemical resistance change sensor, or an optical sensor. In this exemplary embodiment, gas sensor array 12 includes plural gas sensor elements 12a having detection properties that are different from each other. Thus, pattern can be recognized based on a signal output from gas sensor array 12 in response to a volatile organic compound. Gas sensor array 12 includes at least two or more types of gas sensor elements 12a. In order to facilitate the signal processing, gas sensor array 12 can include types of powers of 2, for example, four types, eight types, and sixteen types of gas sensor elements 12a. Gas sensor array 12 may include the same types of gas sensor elements 12a.

Suction device 13 includes an extension pump, a propeller pump, a viscous pump, a reciprocating pump, a rotary pump, a plunger pump, a gear pump, a screw pump, a vane pump, a volute pump, a turbine pump, an axial flow pump, a mixed flow pump, a cascade pump, a diaphragm pump, a sirocco fan, a paddle fan, a turbofan, a mixed flow fan, an axial flow fan, and a transverse flow fan.

Suction device 13 may be implemented by a non-positive displacement pump capable of continuously conveying a large amount of air as the first suction. The non-positive displacement pump can convert the kinetic energy of a rotary machine into the kinetic energy of the conveyed gas, so that the gas can be efficiently conveyed.

Suction device 13 may be implemented by a positive displacement pump capable of quantitatively conveying a small amount of air as the second suction. The positive displacement pump can directly convert energy of a machine into the potential energy of the conveyed gas, so that the self-supply capability is high. Suction device 13 may be implemented by a non-positive displacement pump and a positive displacement pump which are combined with each other. The positive displacement pump performing the second suction preferably has a smaller maximum discharge amount than the non-positive displacement pump performing the first suction.

In order to suppress contamination of an inner surface of suction device 13 with a volatile organic compound, suction device 13 is preferably disposed in the downstream side of housing 11. Suction device 13 may be disposed inside housing 11 because suction device 13 can convey air to gas sensor array 12 efficiently.

Suction device 13 has preferably a flow rate equal to or smaller than 10 L/min and preferably equal to or smaller than a flow rate of 1 L/min so that a sufficient amount of volatile organic compound may be conveyed to gas sensor array 12. In order to reduce the detection time, suction device 13 has a flow rate capable of exchanging almost all air inside housing 11 within 1 minute or less. Suction device 13 may preferably make the pressure of housing 11 to a pressure equal to or larger than an atmospheric pressure, $1.0 \times 10^5$ Pa. In order to obtain a lot of patterns obtained by gas sensor array 12, suction device 13 can reduce the pressure of the inside of housing 11.

At least a part of suction devices 13 can execute suction with little pulsation. By performing suction with little pulsation, another suction to be performed together effectively. The word "little pulsation" means that the instantaneous flow speed shows a substantially constant value with respect to time. For example, a multiple reciprocating pump can be used for reducing the pulsation. Specifically, by shifting the three eccentric axes by 120 degrees each using three diaphragm pumps, the suction waveform sucked from each pump can be made linear. An air chamber or a pulsation attenuator may be used to reduce pulsation. The air chamber is a mechanism that uses the compressibility of the air in the housing to suppress the pulsation of the reciprocating pump and create a stable gas flow.

Suction device 13 may include a non-volumetric axial fan. Since the axial flow fan is continuously sucked by the rotation of the impeller, the pulsation is suppressed.

In the first suction, air occupying most of the air conveyed from the outside of gas sensor 100 to gas sensor array 12 inside housing 11 is sucked through the suction inlet 10. FIG. 2 shows change over time of the instantaneous flow rate in the position of gas sensor array 12. Suction device 13 sucks air of flow rate V1 during the period from time t1 to time t2 as the first suction. Flow rate V1 is preferably constant.

In the second suction, air occupying a part of the air conveyed from the outside of gas sensor 100 to gas sensor array 12 provided inside housing 11 is sucked through suction inlet 10. Suction device 13 sucks air at a flow rate smaller than that of the first suction so that the second suction is performed together with the first suction. As shown in FIG. 2, suction device 13 superimposes the variation of the flow rate ΔV on the first suction during the period from time t1 to time t2, as the second suction. The flow rate ΔV may change periodically at a constant period with respect to time so as to easily detect the gas (see FIG. 2). The flow rate ΔV may change at an irregular period with respect to time. The flow rate ΔV in the second suction may be constant or varied.

The waveform of the second suction may be a triangular wave shown in FIG. 2 or a sine wave shown in FIG. 3. As shown in FIG. 3, in a part of the period of time during which the first suction is performed from time t3 to time t6, the second suction may be performed from time t4 to time t5. The second suction has a monotonously varying flow rate ΔV from time t1 to time t2 as shown in FIG. 4. The second suction may have a monotonously increasing or decreasing flow rate ΔV.

The flow rate V1 sucked as the first suction is smaller than the flow rate ΔV sucked as the second suction. When the ratio ΔV/V1 of the flow rate ΔV to the flow rate V1 is 3 or more, patterns can be easily obtained from gas sensor array 12. The flow rate V1 is determined such that air can be sucked into housing 11 without excess or deficiency and conveyed to gas sensor array 12.

3. Operation

An operation of gas sensor 100 according to this exemplary embodiment, that is, an example of a series of flow of a gas sensing method, will be described below with reference to FIG. 2. Firstly, gas sensor 100 previously prepares the operation of gas sensor 100, and then, starts performing the first suction at time t1. Gas sensor 100 starts performing the second suction after staring performing the first suction. Gas sensor 100 may start performing the first suction and the second suction simultaneously.

After that, during performing the second suction, at measurement point 20a shown in FIG. 2, gas sensor array 12 detects a volatile organic compound included in air. While the second suction is performed, a volatile organic compound can be detected at plural measurement points 20a, 20b, 20c, and 20d. The number of the measurement points are equal to or greater than two. As shown in FIG. 2, patterns 21a, 21b, 21c, and 21d are obtained from gas sensor array 12 at measurement points 20a, 20b, 20c, and 20d, respectively. In patterns 21a, 21b, 21c, and 21d shown in FIG. 2, a black point denotes gas sensor element 12a which reacts to a gas component and outputs a signal, and a white point denotes gas sensor element 12a which does not react to a gas component and which does not output a signal.

The "pattern" in the present disclosure is a collection of responses of gas sensor elements 12a constituting gas sensor array 12. Patterns 21a, 21b, 21c, and 21d are different from each other depending on the flow rate. Some of patterns 21a, 21b, 21c, and 21d may be the same. The response of gas sensor element 12a may be a balanced response or a transient response.

Next, the second suction is ended. Further, the first suction is ended. The first suction and the second suction may be ended simultaneously.

In accordance with this exemplary embodiment, the first suction may be separated from the second suction to detect the volatile organic compound included in air. Therefore, the volatile organic compound included in the air sucked by the second suction is easily detected while the air is sucked into housing 11 by the first suction.

4. Modified Example

Figure 5:
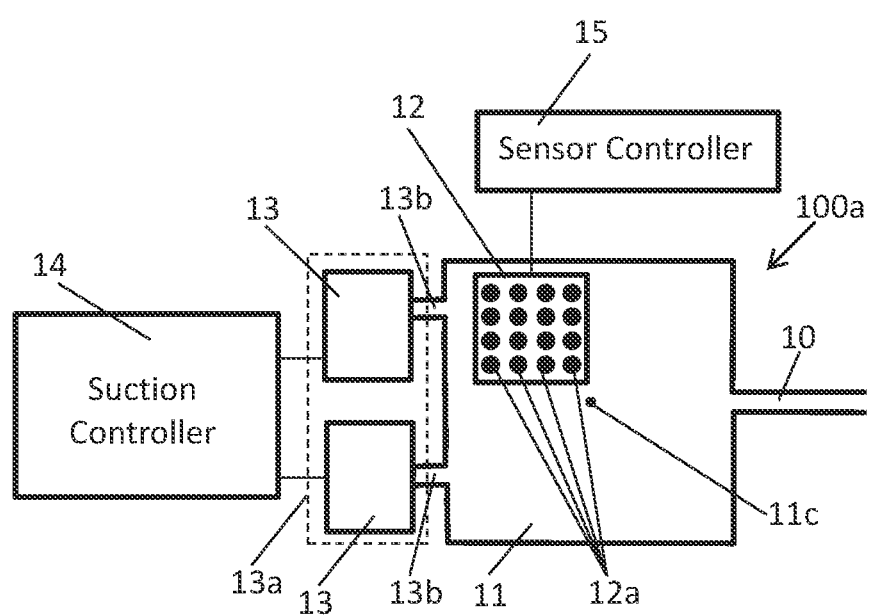
FIG. 5 is a plan view showing an outline of a gas sensor in accordance with a modified example of one exemplary embodiment of the present disclosure.

The above-described exemplary embodiment is only one of various exemplary embodiments of the present disclosure. The above-described exemplary embodiment may be modified variously according to designs and the like as long as an object of the present disclosure can be achieved. Modified examples of the above-described exemplary embodiment will be described below. The following described modified examples may be appropriately combined with one another. FIG. 5 is a plan view showing an outline of gas sensor 100a according to the modified example of an exemplary embodiment of the present disclosure. In FIG. 5, components identical to those of gas sensor 100 shown in FIG. 1 will be denoted by the same reference numerals.

In gas sensor 100a of the present disclosure, suction unit 13a includes plural suction devices 13. Each of the suction devices 13 is coupled to housing 11 through a corresponding one of flow passages 13b to which the each of suction devices 13 communicate. Flow passage 13b may include a valve or a flow-rate control device.

As shown in FIG. 5, gas sensor 100a includes suction controller 14 controlling suction devices 13. Suction controller 14 supplies a sucking control signal to suction device 13 for controlling a state of suction device 13. In accordance with this exemplary embodiment, suction controller 14 controls suction devices 13 in both of the first suction and the second suction, and causes a state to become an operation state in a predetermined time. Suction controller 14 may supply a sucking control signal to one suction device 13 out of plural suction devices 13, thereby controlling performing of the first suction and the second suction. For example, suction controller 14 may control the suction devices 13 such that one suction device 13 performs the first suction at a predetermined flow rate, and the other suction device 13 performs the second suction at a changing flow rate that modulates the first suction.

Gas sensor 100a includes sensor controller 15. Sensor controller 15 supplies a sensor control signal to gas sensor array 12 so as to control a state of gas sensor array 12. Sensor controller 15 may receive an output signal from gas sensor array 12. Sensor controller 15 may be include a memory. The memory includes, for example, electrically writable nonvolatile memories such as Electrically Erasable Programmable Read-Only Memory (EEPROM), and volatile memories such as Random Access Memory (RAM). The memory stores an output signal from gas sensor array 12, an operation of suction device 13, a flow rate at a position of gas sensor array 12, information of a state of air in housing 11, for example, temperature, pressure, humidity, information indicating the type and concentration of the sensed volatile organic compound, at predetermined periods of time.

Gas sensor 100a may include a flow rate sensor. The flow rate sensor may be disposed at an end of suction inlet 10, housing 11, or suction device 13.

Gas sensor array 12 may be located at a position deviated from center position 11c of housing 11, as shown in FIG. 5. Gas sensor array 12 may be located at a position deviated from a line connecting an end surface of suction inlet 10 at a housing 11 to an end surface of suction device 13 at the housing 11. In gas sensor 100 including suction devices 13, gas sensor array 12 may be located in a vicinity of one suction device 13.

Suction device 13 may suck a gas for comparison in order to compare the gas for comparison with air including a volatile organic compound to be detected. The "gas for comparison" in the present disclosure may be a gas obtained by allowing the sucked gas to pass through a filter, or a gas obtained by sucking from suction inlet 10. Furthermore, the "gas for comparison" in the present disclosure may be a gas previously stored in a container. The gas for comparison is, for example, clean air, nitrogen gas, and helium gas. Suction device 13 may suck the comparison gas by the first suction and the second suction. Gas sensor array 12 may acquire a pattern for the gas for comparison sucked by the first suction and the second suction. Gas sensor array 12 may detect a volatile organic compound included in the gas for comparison sucked by the first suction and the second suction.

5. Summary

As described above, a gas sensor according to a first aspect includes a suction inlet, a housing, a gas sensor array, and a suction unit. The suction unit is configured to perform a first suction conveying a gas component in air to the gas sensor array through the suction inlet together with a second suction conveying the gas component to the gas sensor array at a flow rate smaller than a flow rate of the first suction. The gas sensor array is configured to operate while the suction unit performs the second suction.

This aspect provides an advantage that the detection accuracy of a gas component to be sensed, that is, a volatile organic compound is easily improved.

In a gas sensor according to a second aspect, the suction device is one of plural suction devices, and at least one suction device among the suction devices performs the second suction.

This aspect provides an advantage that, since a flow with a flow rate smaller than that of the first suction can be formed by at least one suction device, air can be sucked easily.

In a gas sensor according to a third aspect, the gas sensor array acquires plural patterns with respect to the gas component included in air sucked in the second suction.

This aspect provides an advantage that, since the gas sensor array can acquire plural patterns, the detection accuracy can be improved.

In a gas sensor according to a fourth aspect, a suction controller that controls an operation state of the suction device supplies a signal to a sensor controller for controlling the gas sensor array.

This aspect provides an advantage that patterns can be efficiently acquired by the gas sensor array by reflecting the operation state of the suction device.

In a gas sensor according to a fifth aspect, the suction device sucks air including a gas component, and a gas for comparison to be used for comparison with air.

This aspect provides an advantage that, since a gas component can be detected based on the gas for comparison, the detection accuracy can be improved.

The configurations in accordance with the second to fifth aspects are not essentially required for the gas sensor, and can be appropriately omitted.

INDUSTRIAL APPLICABILITY

A gas sensor according to the present disclosure is useful for detection of various types of gases or odors.

REFERENCE MARKS IN THE DRAWINGS

100 gas sensor
10 suction inlet
11 housing
12 gas sensor array
13 suction device
14 suction controller
15 sensor controller
20a, 20b, 20c, 20d measurement point
21a, 21b, 21c, 21d pattern

The invention claimed is:

1. A gas sensor comprising:
    a suction inlet;
    a housing communicating with the suction inlet;
    a gas sensor array disposed in an inside of the housing; and
    a suction unit disposed at an end of the housing and configured to suck a gas component inside of the housing in which the gas sensor array is disposed, wherein:
    the suction unit is configured to:
        perform a first suction conveying the gas component in the air to the gas sensor array through the suction inlet at a first flow rate, and
        perform a second suction conveying the gas component to the gas sensor array at a second flow rate, the second flow rate is smaller than the first flow rate,
    the suction unit is configured to perform the second suction together with the first suction, and
    the gas sensor array is configured to operate while the suction unit performs the second suction.

2. The gas sensor according to claim 1, wherein the suction unit includes:
    a first suction device configured to perform the first suction, and
    a second suction device configured to perform the second suction,
    wherein the first suction device and the second suction device are connected to the housing in parallel.

3. The gas sensor according to claim 1, wherein
    the gas sensor array includes a plurality of gas sensor elements, and
    the gas sensor array is configured to acquire a plurality of patterns, each of the plurality of patterns indicating one or more gas sensor elements which react with a gas component included in air sucked by the second suction, the one or more gas sensor elements being included in the plurality of gas sensor elements.

4. The gas sensor according to claim 1, further comprising:
a sensor controller configured to control the gas sensor array; and
a suction controller configured to control an operation of the suction unit and to supply a signal to the sensor controller.

5. The gas sensor according to claim 4, wherein
the suction controller is configured to control both of the first suction and the second suction.

6. The gas sensor according to claim 1, wherein the suction unit is configured to suck the air including the gas component and suck a gas for comparison to be used compared with the air.

7. The gas sensor according to claim 1, wherein
the first flow rate is constant, and the second flow is constant or varied.

8. The gas sensor according to claim 7, wherein
a waveform of the second suction is a triangular wave, a sine wave or a monotonous form.

9. A gas sensor comprising:
a suction inlet;
a housing communicating with the suction inlet;
a gas sensor array disposed in an inside of the housing; and
a suction unit disposed at an end of the housing, wherein:
the suction unit includes a non-positive displacement pump and a positive displacement pump, and
the positive displacement pump has a maximum discharge amount smaller than a maximum discharge amount of the non-positive displacement pump.

10. The gas sensor according to claim 9, wherein the non-positive displacement pump and the positive displacement pump are connected to the housing in parallel.

11. The gas sensor according to claim 9, further comprising a suction controller, wherein the suction controller is configured to control the non-positive displacement pump at a predetermined first flow rate and to control the positive displacement pump at a changing flow rate smaller than the first flow rate.

* * * * *